United States Patent [19]
Yap

[11] Patent Number: 6,113,532
[45] Date of Patent: Sep. 5, 2000

[54] EJACULATION AID AND SPERM COLLECTION DEVICE

[76] Inventor: Joseph Karl Yap, P.O. Box 1513, Kingston 8, Jamaica

[21] Appl. No.: 09/310,033

[22] Filed: May 11, 1999

Related U.S. Application Data

[60] Provisional application No. 60/085,768, May 16, 1998.
[51] Int. Cl.$^7$ .................................................. A61F 5/00
[52] U.S. Cl. ................................................................ 600/38
[58] Field of Search ........................... 600/38, 39, 41, 600/33, 35, 573; 604/346, 347, 349, 352–355; 128/844, 883, 885

[56] References Cited

U.S. PATENT DOCUMENTS 5,331,974   7/1994  Sook .
5,458,559  10/1995  Gauntlett ................................... 600/38
5,836,865  11/1998  Ritchie et al. .

*Primary Examiner*—Cary O'Connor
*Assistant Examiner*—Catherine McPherson
*Attorney, Agent, or Firm*—John V. Stewart

[57] ABSTRACT

A multi-chambered balloon formed from a single rectangular plastic sheet, with an inflated shape approximating a vagina with adjustable tightness and a seamless opening. Manufacturing steps are minimized and simplified to one cutting operation, one valve insertion, and three seams. This minimizes cost, allowing a sex aid that is disposable for maximum cleanliness.

3 Claims, 2 Drawing Sheets

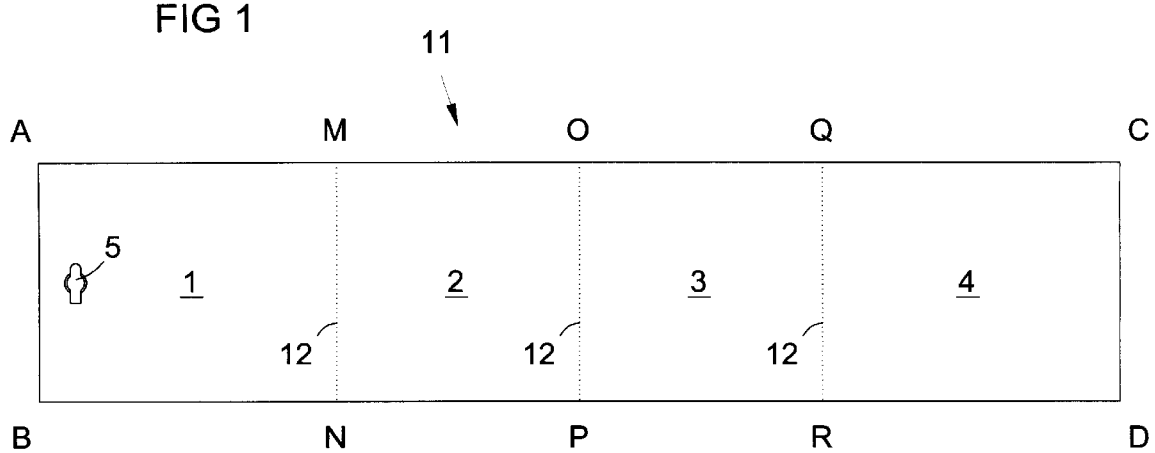
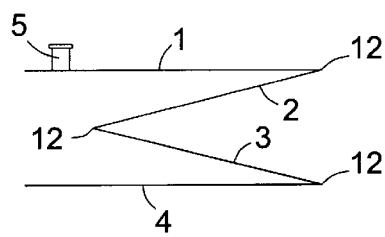
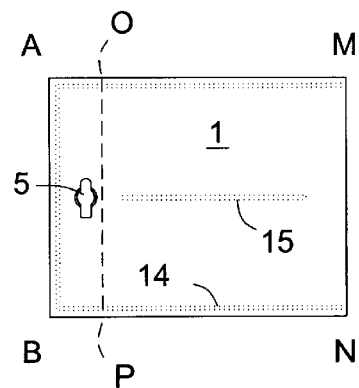

EJACULATION AID AND SPERM COLLECTION DEVICE

CROSS-REFERENCE TO RELATED APPLICATIONS

This application claims the benefit of U.S. Provisional Application No. 60/085,768 filed May 16, 1998.

BACKGROUND OF THE INVENTION

1. Field of the Invention

This invention is in the field of sex aids for men.

2. Description of Prior Art

Sex aids for men are numerous in the prior art, but often are impractical or expensive to manufacture, store, or use. Two examples of related inventions are described in the patents below.

U.S. Pat. No. 5,331,974 (Sook) shows a Multi-Purpose Sexual Device with Disposable Condom Usage. It is an elongated flexible cup designed to be inserted into a vagina and receive a penis for safe intercourse, providing contraception and disease prevention. It has an inflatable portion for adjusting the pressure on the penis. It is substantially more complicated to manufacture than the present invention. It has inwardly protruding seamed edges (1) and a seamed edge (1') all around the opening, both of which can irritate the penis.

U.S. Pat. No. 5,836,865 (Ritchie et al.) shows a Male Sex Aid. It is a tube made of three elongated fluid chambers forming a long open-ended artificial vagina. Each chamber has at least one fluid valve. This device requires at least 4 seams, at least three fluid valves, and it has a seam all around the opening that can irritate the penis. It is open-ended, so it cannot retain semen. In contrast, the present invention only requires 3 seams and 1 fluid valve, has no seam around the opening, and retains semen.

SUMMARY OF THE INVENTION

The object of the present invention is a basic ejaculation aid that is safe, effective, and inexpensive. The emphasis is on optimizing manufacture to minimize the production cost of a comfortable inflatable ejaculation aid. A further object is minimal size in storage.

This object is met in a multi-chambered balloon formed from a single rectangular plastic sheet, with an inflated shape approximating a vagina with adjustable tightness and a seamless opening. Manufacturing steps are minimized and simplified to one cutting operation, one valve insertion, and three seams. This minimizes cost, allowing a sex aid that is disposable for maximum cleanliness. The device can be folded flat or rolled to a minimal storage size.

BRIEF DESCRIPTION OF THE DRAWINGS

FIG. 1 Top view of plastic sheet with fold-lines

FIG. 2 Side view of folded plastic sheet before sealing

FIG. 3 Top view of folded plastic sheet with an edge seam (14) sealing all panels (1–4) around three edges. A central seam (15) connects panels 1 and 2, and another central seam (not shown) likewise connects panels 3 and 4.

REFERENCE NUMERALS

Figure 4:
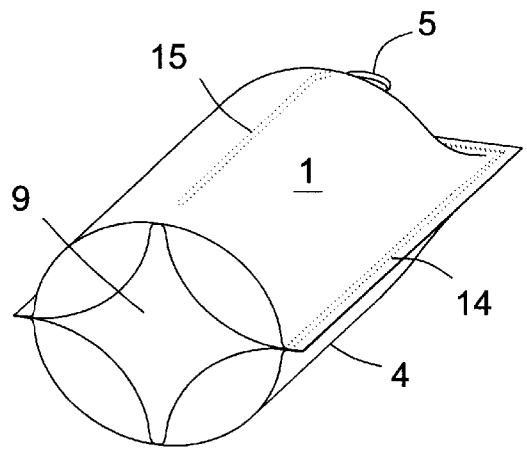
FIG. 4 Perspective view of inflated device
Figure 5:
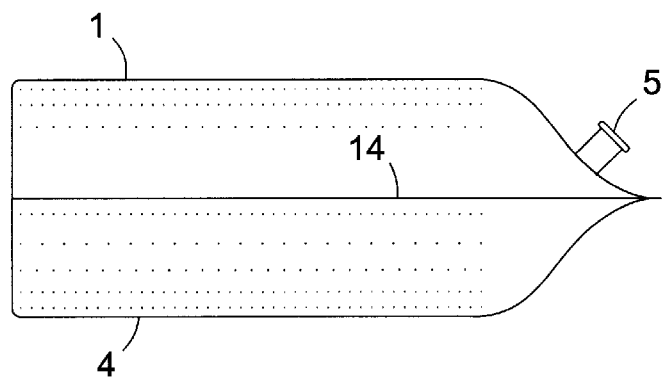
FIG. 5 Side view of inflated device
Figure 6:
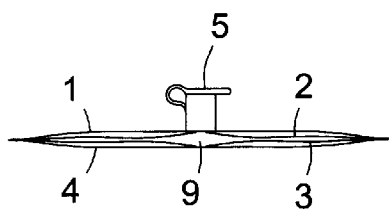
FIG. 6 Front sectional view of deflated device

1. Panel 1
2. Panel 2
3. Panel 3
4. Panel 4
5. Air valve
9. Cavity
11. Plastic sheet
12. Fold-line
14. Edge seam
15. Center seam

DESCRIPTION

The ejaculation aid is made from flexible sheet material, such as vinyl plastic. It is inflated for operation. In the deflated position, the device is flat, and can be conveniently stacked, folded, or rolled for storage. The preferred construction method comprises the following steps:

1. Cut a smooth rectangular plastic sheet as represented in FIG. 1 by corners A, B, C, and D. Locations for folds are shown as dotted lines (12). Lengths AM, BN, QC, and RD are equal to each other. Lengths MO, NP, OQ, and PR are equal to each other. Length AM is greater than length MO.
2. Insert an air valve (5) centered a short distance from edge AB.
3. Fold the plastic along lines (12) as shown in FIG. 2.
4. Create center seams (15) as in FIG. 3 between panels 1 and 2, and between panels 3 and 4 by heating or other conventional means.
5. Create an airtight edge seam (14) around three edges of the folded plastic as in FIG. 3 by heating or other conventional means.

Figure 7:
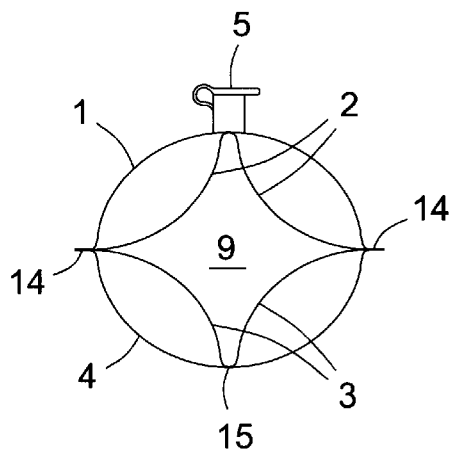
FIG. 7 Front sectional view of inflated device

This results in an airtight plastic shell, which can be inflated, resulting in a frontal cross section as shown in FIG. 7. A cavity (9) is open at the front end of the device for insertion of the penis. In use, the device is inflated to a moderate pressure. The penis is inserted in the cavity (9) between the air chambers, and stimulated by sliding the device on the penis. The outer walls (1 and 4) of the device can be manually squeezed during use to achieve the desired pressure.

The device serves as a stimulator and as a receptacle for semen. The device can be used as an aid for treating erectile dysfunction. It is designed for low manufacturing cost, and is intended to be disposable, although it can be washed and reused if desired. The walls of the cavity provide even pressure around the penis. The opening of the cavity is seamless, being formed by folds rather than seams, thus avoiding irritation caused by seams. In use, no seams touch the penis.

Although the present invention has been described herein with respect to preferred embodiments, it will be understood that the foregoing description is intended to be illustrative, not restrictive. Modifications of the present invention will occur to those skilled in the art. All such modifications that fall within the scope of the appended claims are intended to be within the scope and spirit of the present invention.

I claim:

1. An ejaculation aid and sperm collection device for men, comprising:

an elongated piece of flexible film having a length subdivided by first, second, and third substantially parallel fold lines, the second fold line being substantially central in the length of the film, said fold lines defining first, second, third, and fourth contiguous panels, the first and fourth panels outermost, the second and third panels contiguous at the central fold line;

the film folded on said fold lines into a substantially W-shaped side view, then flattened therefrom into a four-layered sheet having four peripheral edges;

the first and fourth panels being longer than the second and third layers, the first and fourth panels extend beyond the second fold line to contact each other in the layered sheet;

a first seam connecting a portion of the first and second panels together along a line substantially medial to and perpendicular to the fold lines;

a second seam connecting a portion of the third and fourth panels together along a line substantially medial to and perpendicular to the fold lines;

a continuous seam around three of the peripheral edges of the folded layered sheet, excepting the fold lines, thus forming a first envelope between the first and second panels, a second envelope between the third and fourth panels, and an air communication path between the two envelopes; and an air valve in at least one of the outer panels for inflating the envelopes;

whereby a multi-chambered inflatable balloon is formed from a single sheet of film, having an inflated shape approximating a vagina, with adjustable tightness and a seamless opening.

2. A method of constructing an ejaculation aid and sperm collection device, comprising the steps of:

a) cutting a plastic sheet into substantially a rectangle having first and second long edges and first and second short edges;

b) inserting an air valve in the sheet adjacent one of the short edges;

c) folding the plastic sheet into substantially a W-shaped side view, along three fold lines in the sheet, the fold lines substantially parallel to the short edges, thereby defining first, second, third, and fourth sequentially contiguous panels in the sheet;

d) creating a first center seam that seals the first and second panels together along a line substantially equidistant between the long edges of the sheet;

e) creating a second center seam that seals the second and third panels together along a line substantially equidistant between the long edges of the sheet; and f) creating an air-tight edge seam that seals the short edges together and seals each folded long edge against itself across all adjacent layers of the folded sheet;

whereby a multi-chambered inflatable balloon is formed from a single sheet of film, having an inflated shape approximating a vagina, with adjustable tightness and a seamless opening.

3. A method of constructing an ejaculation aid and sperm collection device, comprising the steps of:

a) cutting a plastic sheet into approximately a rectangle with first and second short edges, first and second long edges, and a length being the distance between the short edges;

b) folding the plastic sheet into substantially a W-shaped side view along three fold lines in the sheet, the fold lines being substantially parallel to the short edges, including a central fold line substantially equidistant from the two short edges, and including second and third fold lines substantially equidistant from the central fold line and on opposite sides thereof, the fold lines defining first and second central panels adjacent the central fold line and first and second outer panels adjacent the respective inner panels, the outer panels being longer than the inner panels;

c) inserting an air valve in the sheet adjacent one of the short edges of the sheet;

d) creating a center seam between the first inner and the first outer panel, and creating a center seam between the second inner and the second outer panel, the center seams following a line substantially medial between the long edges of the sheet;

e) flattening the W-shaped folded sheet into a 4-layer flat sheet in which the two short edges of the original sheet are adjacent, and f) creating an air-tight edge seam between the short edges of the sheet, and along the folded long edges of the sheet;

whereby a multi-chambered inflatable balloon is formed from a single sheet of film, having an inflated shape approximating a vagina, with adjustable tightness and a seamless opening.

* * * * *